United States Patent

Rogers et al.

[11] Patent Number: 5,107,824
[45] Date of Patent: Apr. 28, 1992

[54] ANATOMICALLY CORRECT KNEE BRACE HINGE

[75] Inventors: Michael M. Rogers; Linda L. Rogers, both of Mountain View, Calif.

[73] Assignee: Anodyne, Inc., Boulder, Colo.

[21] Appl. No.: 407,185

[22] Filed: Sep. 14, 1989

[51] Int. Cl.[5] .................................. A61F 5/00
[52] U.S. Cl. .................................. 602/16; 602/26
[58] Field of Search .............. 128/80 C, 80 R, 77, 128/88, 80 F; 623/27, 32, 39, 45

[56] References Cited

U.S. PATENT DOCUMENTS

| | | | |
|---|---|---|---|
| 1,390,915 | 9/1921 | Loth | 623/27 X |
| 3,779,654 | 12/1973 | Horne | 128/80 C X |
| 3,902,482 | 9/1975 | Taylor | 128/88 X |
| 4,361,142 | 11/1982 | Lewis et al. | 128/80 C |
| 4,463,751 | 8/1984 | Bledsoe | 128/80 C |
| 4,723,539 | 2/1988 | Townsend | 128/80 C |

FOREIGN PATENT DOCUMENTS

2600528 12/1987 France .................. 128/80 C

Primary Examiner—Richard J. Apley
Assistant Examiner—Lynne A. Reichard

[57] ABSTRACT

An improved hinge design for an articulating knee brace utilizing nested spherical hinge cups to accurately mimic the actual movement of the human knee. The movements of flexion/extension, rotation, abduction/adduction, and rollback and glide are tracked by the brace during knee movement through the use of slots and rivets to manipulate the relationship between upper and lower brace structures to support the knee in its natural positions.

14 Claims, 5 Drawing Sheets

FIG.10A
0° FLEXION
(FOOT ORIENTATION)
MEDIAL LATERAL

FIG.10B
30° FLEXION

FIG.10C
90° FLEXION

FIG.10D
140° FLEXION
10mm  24mm

ANATOMICALLY CORRECT KNEE BRACE HINGE

BACKGROUND OF THE INVENTION

Many brace devices have been advanced to provide control for the movement of the human knee after injury, during recuperation after injury, and to optimize the protection and healing thereof. Prior devices have exhibited a conspicuous absence of satisfactory understanding of knee anatomy and especially knee kinematics. In order to appreciate the full worth of this invention, a general understanding of knee anatomy and kinematics is desirable.

The knee joint includes three bones, the patella, the femur and the tibia. The distal end of the femur consists of a bicondylar structure which refers to the two blunt projections, known as "condyles", forming the lower end of the femur. These two condyles, medial (inner) and lateral (outer), are asymmetrically cam-shaped. The proximal end of the tibia is comprised of a specialized surface termed the tibial plateaus upon which the corresponding condyles articulate.

Unlike the hip joint, where the contour of the joint is a primary stabilizing factor, a primary stabilizing factor in the knee is the surrounding supporting tissue such as the fibrous capsule with its specialized components, the capsular ligaments and the menisci. Most important to stabilization in the knee, are the two intra-articularly located cruciate ligaments.

Knee stability can be considered in terms of static and dynamic stability. The above-noted structures are important in both instances, but during motion, certain muscle units become increasingly important, not only in terms of knee joint stability, but also in terms of carrying out the normal knee kinematics.

The mechanical axis of the lower limb can be said to extend from the center of the femoral head to the center of the ankle joint, passing near to the center of the knee. The true vertical axis is a line that extends from the center of gravity of the body down in the direction of gravity in a plane perpendicular to gravity. In the normally aligned lower limb, the mean mechanical axis of the leg is angled 3 degrees toward the true vertical axis. The femoral shaft is angled downward approximately 9 degrees toward the vertical axis and the tibia is angled approximately 6 degrees outward (valgus) with relationship to the femur.

The knee is a complex joint with multiple movements. Anatomically, the knee is classified as a diarthrodial joint of the ginglymus (hinge) type; however, even this broad definition does not do justice to the complex series of movements that occur during normal knee motion.

The ginglymus connotation refers to the flexion and extension movement, but flexion and extension do not occur about a fixed transverse axis but rather about a constantly changing center of rotation. This particular aspect of knee motion has been appropriately labeled "polycentric rotation". This phenomenon, however, considered by itself, falls short of describing the kinematics of the human knee.

During flexion and extension in the sagittal plane, simultaneously abduction and adduction are occurring in the coronal plane and internal rotation and external rotation are occurring in the transverse plane. To carry the complexity further is the phenomenon of combined rolling and gliding motio of the femoral condyles on the tibial plateaus. Rolling motion determines the "rollback" of the femur on the tibia during flexion. The ratio of rolling to gliding motion differs in the lateral compartment compared to the medial. This kinematic fac gives rise to the phenomenon known as "differential roll-back."

The knee joint is often times subjected to a loading force equal to several times the body weight in level walking. These forces increase with running or other "impact loading" activities. Loads are not transmitted over the joint surface equally but rather over a relatively small area of each femora condyle and the tibial plateau. The medial side of the joint bears a larger load than the lateral; but the medial plateau is also larger than the lateral; therefore, the force per unit ar is approximately equal.

The configuration of the femoral condyles is asymmetric. The lateral condyle is broader in the sagittal an transverse planes than the medial condyle The medial condyle projects distally to a level slightly lower than the lateral. This distal projection helps to compensate for the varus (toward) inclination in the femur with respect to the vertical axis. As a result, in the erect, in-line position, the transverse plane of the condyles lies near the horizontal.

As the knee approaches full extension, it can be considered that the femur rotates internally (as concurrently the tibia is rotating externally) allowing the anterior articular surface of the medial femoral condyle to come in contact with the anterior portion of the medial tibial plateau. The lateral condyle moves anteriorly (forward) more rapidly than the medial, thus producing the phenomenon of the "screw home mechanism", until the knee is "locked" in the fully extended position. This rotary movement passes through a series of polycentric axes.

The workers in the prior art have utilized a variety of hinge members in an attempt to track the sliding and roll-back of the condyles with respect to the tibia plateaus. However, none of the prior art has accomplished an external knee hinge mechanism that accounts simultaneously for the differential roll-back, the rotation of the tibia with respect to the femur during flexion and extension, and the abduction/adduction movement that occurs concurrently with the other movements. A preferred embodiment of this invention has accomplished this through a series of slotted curvilinear shells all of which have their concave surfaces facing in the same direction.

FIELD OF THE INVENTION

This invention relates to a hinge mechanism that tracks the aforementioned complex movements of the knee when the hinge is used with leg bracing.

A principal objective of this invention is to provide better protection to the knee, to allow for better healing of an injured knee and/or to protect the knee during sports activity. The hinge is utilized with bracing designed for the aforementioned activities.

It is another principal objective of this invention to provide a knee brace having novel hinging that improves the prior art by providing apparatus that accurately reflects average normal knee behavior so as to reduce the strain on all connecting elements of the knee during recuperation.

Another important objective of the invention is to provide a novel hinging arrangement which can be used on devices that permit normal knee movement over a selected portion of the knee's flexion and extension capability.

Another important objective of the invention is to provide a novel hinge mechanism that utilizes a series of curved shells, all of which are facing in the same direction, which positioning maximizes the ability of the brace to track knee movements anatomically, including the rotation, the abduction/adduction, and the differential roll back movements.

Still another important objective of this invention is to provide a hinge for use with a bracing mechanism having means to engage the tibia section of the leg and means to engage the femur section of the leg, with an interconnecting hinge arrangement on either side of the knee, to permit limited flexion and extension of the knee motion, in an adjustable manner Another objective of this invention, because of its relative simplicity, lightweight design and its ability to track normal knee movement, is to provide an accident-preventative apparatus for use by athletes whose legs are subjected to severe stresses; and by the athlete who has pre-existing ligament and cartilage injury that must be protected.

Another objective of this invention is to provide a hinging arrangement that includes a series of cup-shaped elements which are used in conjunction with slots formed therein to accurately track the anatomical movement of the knee during flexion and extension.

Another objective of this invention is to provide hinging that is uniquely designed to allow for polyaxial, multi-planar, asymmetrical movement.

These and other objectives of this invention can be more readily understood by reference to the attached specification and drawings.

SUMMARY OF THE INVENTION

The brace of this invention provides a mechanism to accurately track the anatomical motion of the human knee. This anatomical tracking, when used with bracing, protects the knee and reduces stress on the anatomical parts of the knee, particularly the ligaments.

Treatments for which the brace is used include, among other applications, rehabilitation following surgery to the knee, protection for an injured or surgically repaired knee, and protection for an uninjured knee Its use will be applicable for most types of surgical repairs to the knee and in the prevention of many types of damage to the knee. The brace of this invention and its unique hinging apparatus permits movement of four distinct types in three dimensions simultaneously.

DESCRIPTION OF THE PREFERRED EMBODIMENT

Figure 1:
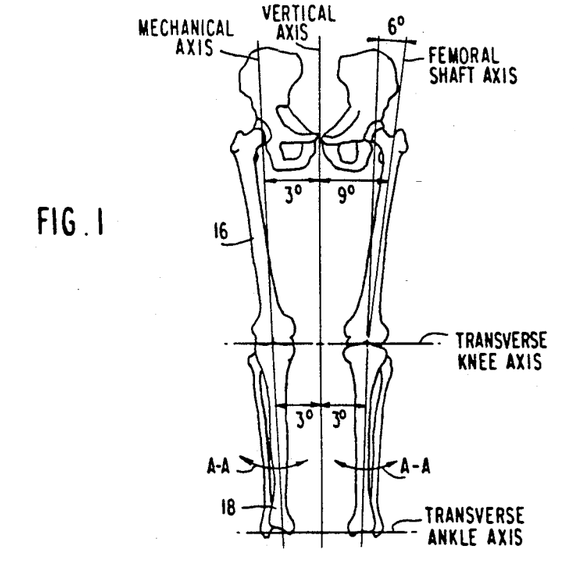
FIG. 1 is a front view of the skeletal framework of the lower body showing femoral, tibial, and mechanical axes angles with respect to the vertical.

FIG. 1 is a diagrammatic front elevation showing the leg components and their relationship with one another. As shown, the approximate mechanical axis of the normal or average human leg extends from the center of the hip joint to the center of the ankle joint and passes near to the center of the knee. This axis of the leg is angled 3 degrees toward the vertical axis of the body. The femur shaft axis is directed at an angle of 9 degrees toward the true vertical axis of the body and the tibia is aligned with the mechanical axis which is directed 3 degrees toward the vertical axis of the body. Thus, there is approximately a 6° outward (valgus) angle between the femur and the tibia in the mean configuration of a human knee.

Figure 2:
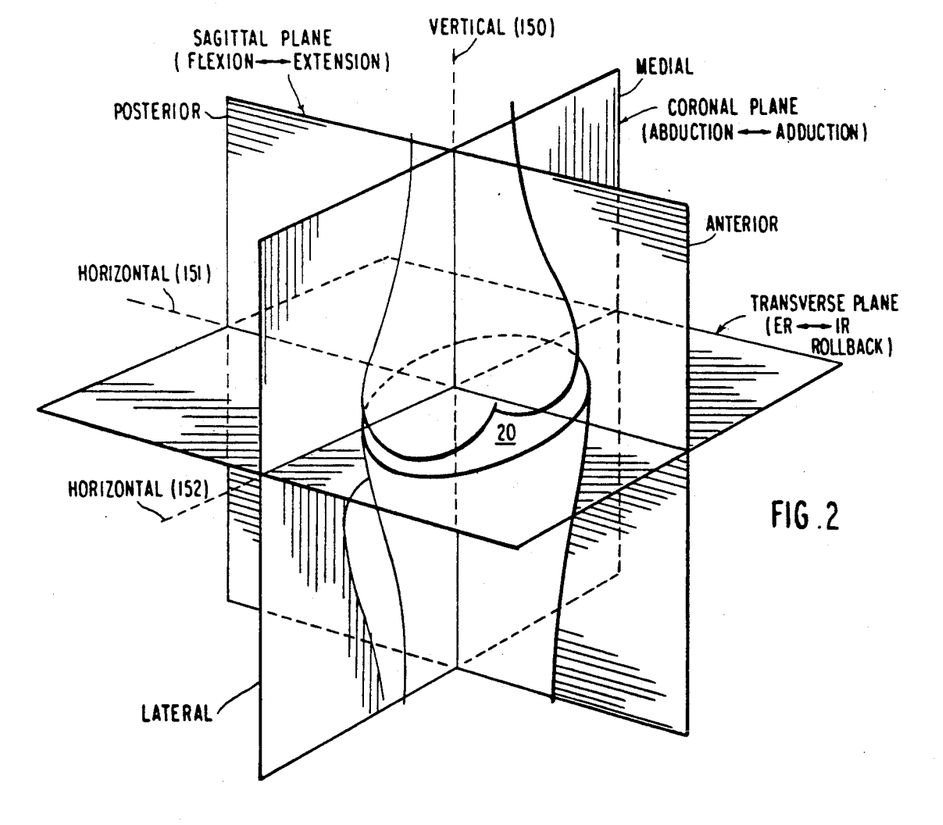
FIG. 2 is a perspective of the knee joint with the sagittal, coronal and transverse planes related thereto.

FIG. 2 discloses the knee joint in perspective and superimposes three perpendicular planes therethrough; namely, the sagittal plane in which flexion-extension movements occur; the transverse plane in which rollback and rotational movements occur; and the coronal plane in which abduction and adduction occurs. Movements are concurrent but it is convenient for purposes of description to identify the planes in which the principal components of movement take place.

Referring now to the other drawings wherein like numerals refer to like parts, the numeral 10 refers to the brace of this invention. An essential component of the brace is its hinging apparatus, two principal elements of which are an outer or "lateral" hinge 12 and an inner or "medial" hinge 14. In this description, only the brace and hinge mechanism for the left leg is described. It is to be understood, of course, that the brace for the right leg will be a mirror image of that described herein.

Figure 6:
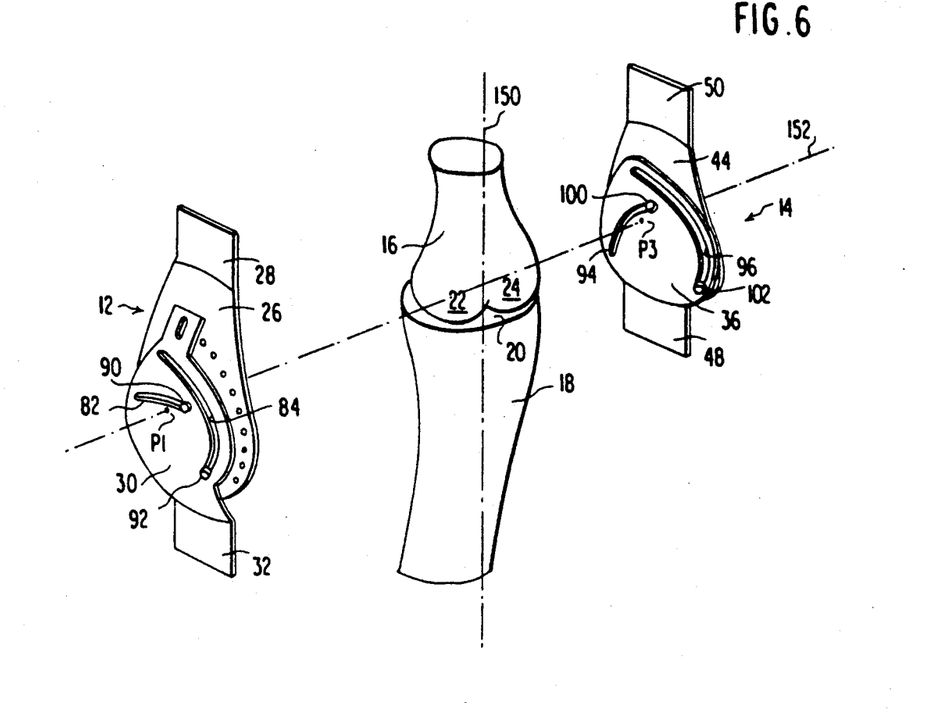
FIG. 6 is an exploded, diagrammatic-schematic perspective view of the hinge at the normal or full extension position of the leg.

The femur of the wearer is indicated by the numeral 16 and the tibia by numeral 18 in FIG. 6. At its upper end, the tibia has two generally planar or plateau surfaces indicated jointly by the numeral 20. The plateaus are curved slightly but for purposes of this description are shown as generally flat in FIGS. 6 and 7. The lower end of the femur is bicondylar and is formed with a generally cam shaped lateral condyle 22 and a generally cam shaped medial condyle 24. The lateral condyle 22 is larger than the medial condyle 24.

The lateral hinge 12 (FIGS. 5 and 5A) is comprised of an inner shell or cup 26 having an extension 28 that is generally parallel to the femur and an outer shell 30 having a downwardly directed extension 32 that is generally parallel to the tibia. The outer shell 30 has an inner curvilinear surface 31 having the same radius of curvature as, and mates with, the outer spherical surface 34 of shell 26.

The medial hinge 14 (FIGS. 4 and 4A) has an inner shell 36, the convex surface 38 of which is placed adjacent the knee. The concave surface 40 of shell 36 mates with the convex surface 42 of a medial shell 44. All of the above-defined spherical surfaces have approximately the same degree of curvature and are facing in the same direction; that is, for the right leg, the concave surfaces 40 and 44 face to the left of the leg, and for the left leg, the concave surfaces face to the right of the leg. The shell 36 has a downwardly directed extension member 48 and the shell 44 has an upwardly directed extension member 50. The extensions 28, 32, 48 and 50 provide anchoring means for brace shafts 116, 118, 136, 138.

Figure 5:
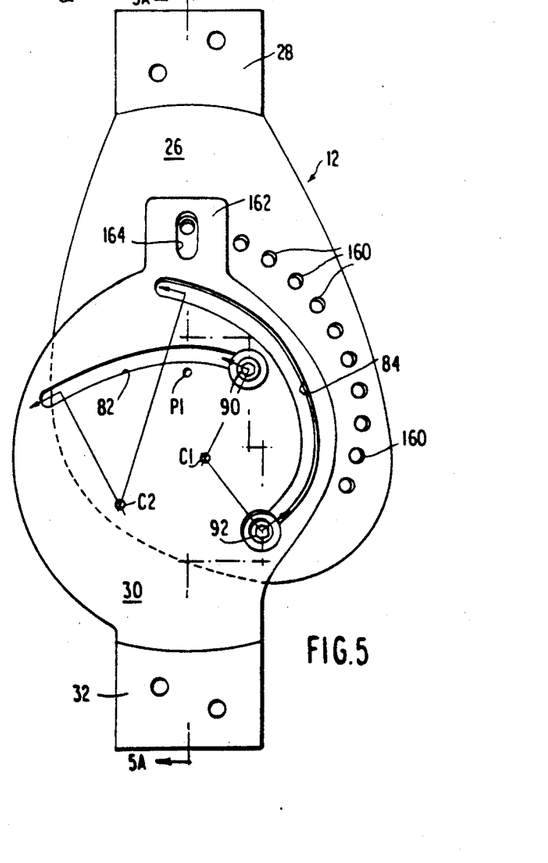
FIG. 5 is a side exterior elevational view of the lateral (outer) leg hinge component of FIG. 3.
Figure 5A:
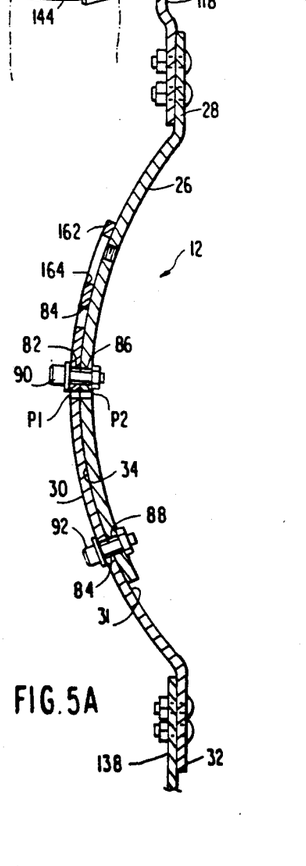
FIG. 5A is a cross-sectional view along the line 5A—5A of FIG. 5.

As seen in FIGS. 5 and 5A, the outer shell 30 of lateral hinge 12 is formed with a generally horizontal, slightly curved, slot 82 and a generally vertical, curvilinear slot 84. Shell 26 is formed with a pair of openings 86 and 88 in which a pair of rivets 90 and 92 are received. The rivets 90 and 92 respectively extend through slots 82 and 84 in sliding engagement. The rivets secure shell 26 in close sliding engagement with shell 30. The rivets can be formed with headed ends or can take the form of a headed nut and screw. The rivets are stationary with respect to shell 26. Shell 30 moves relative to the rivets along a course defined by slots 82 and 84.

The inner shell 36 of the medial hinge 14 (FIG. 4) is formed with a generally vertical, slightly curved, slot 94 and a curvilinear slot 96. The slot 96 extends from a generally vertical straight position to a generally straight horizontal position with an arcuate position therebetween. The shell 44 is formed with openings 98 and 99 (not shown, in FIG. 4a but similar to openings 86 and 88) in which rivets 100 and 102 are received. Rivets 100 and 102 are also received respectively by slots 94 and 96. The rivets secure shell 44 and shell 36 together. These rivets can also be formed with heads or with nut and bolt arrangements In either event, the rivets are stationary with respect to shell 44, shell 32 moves along a course defined by slots 94 and 96. Three-dimensional movement of the knee brace is governed by the shapes of the slots and the spherical shape of the shells.

As stated above, the mating surfaces of the shells have approximately the same radius of curvature. The radii are close enough to permit a close sliding engagement. In the disclosure, the reference apices of these curves are represented by the pinholes P1, P2, P3 and P4 respectively formed in the shells 30, 26, 36 and 44. When the brace 10 is secured to the leg of a wearer in its extended or unflexed position, pinholes P1, P2, P3 and P4 are coaxially aligned on the transverse axis of the condyles 22 and 24 as shown in FIG. 6. See axis 152.

The aforementioned hinge elements 12 and 14 form the movable portion of brace 10. Although hidden in FIG. 6, P2 and P4 are directly behind P1 and P3 respectively. At its upper end, brace 10 includes a pair of opposing plastic cuffs 110 and 112 to grasp the thigh of a wearer. Between the cuffs and the leg is a foam padding 114.

Extending upwardly from extension 50 and connected thereto is a bracing shaft 116 that is fixedly secured to cuff 112. Extending upwardly from extension 28 of shell 26 is a bracing shaft 118 that is fixedly secured to cuff 110. Circumscribing the cuffs and shafts are a pair of straps 120 and 122. The straps can have a buckle or be equipped with a Velcro fastening means. After the cuffs are placed about the thigh, the straps 120 and 122 are tightened so as to provide a snug fit. A pair of retainers 124 and 126 connect the cuff units to reduce rotational slippage between the thigh and the cuffs. It should be noted here that extensions 116 and 118 are aligned with one another and the femur. Respective movement among these members and the femur is not desirable. The purpose of the cuffs and upper bracing is to minimize such respective movement.

At its lower end, the brace 10 includes a pair of opposing plastic cuffs 130 and 132 that grasp the lower leg therebetween. Extending downwardly from extension 48 is an inner tibia limb brace 136 and extending downwardly from extension 32 is an outer tibia limb brace 138. The braces 136 and 138 are respectively secured to cuffs 132 and 130. A foam padding 134 is disposed between the rigid cuffs and the lower leg. The cuffs 130 and 132 are retained in a close and snug engagement with the lower leg by buckled belts or straps 142 and 144 similar to straps 120 and 122. These four straps can also be equipped with Velcro surfaces. As noted with respect to the femur above, this system of cuffs and braces is intended to minimize movement between the wearer's leg and the brace structure.

Figure 10A:
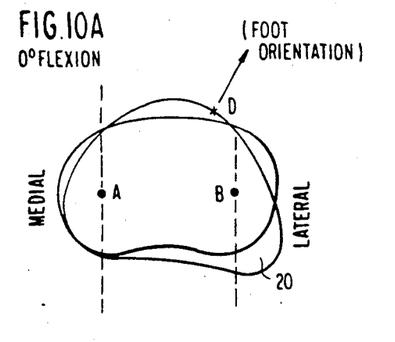
FIGS. 10A through 10D are further diagrammatic representations of knee positions during various phases of flexion.

As noted above, the knee is a complex joint which exhibits of several distinct movements occurring simultaneously. It is the ability of the present invention to accommodate these movements which allows close tracking of the anatomical movement of the human knee. These movements can be reduced to four basic types consisting first of the flexion/extension movement in the sagittal plane (FIG. 2); second, the internal/external rotation movement in the transverse plane (FIG. 2); third, the abduction/adduction movement in the coronal plane; fourth, "rollback", is a combination of the rolling motion and the gliding (spinning) motion of the femur on the tibia in the transverse plane (FIGS. 10 A'–100")

The first element of flexion and extension is the rotation (swinging) of the tibia about the transverse condylar axis 152. Rather than simple mechanical hinging about this axis, the tibia undergoes polycentric motion travelling about a continuously changing center of rotation as flexion progresses. The tibia does not in fact swing about the condylar axis but rather rotates about a point which changes as a function of the flexion angle. As such, a simple pin hinge design knee brace fails to accommodate this polycentric movement.

Figure 7:
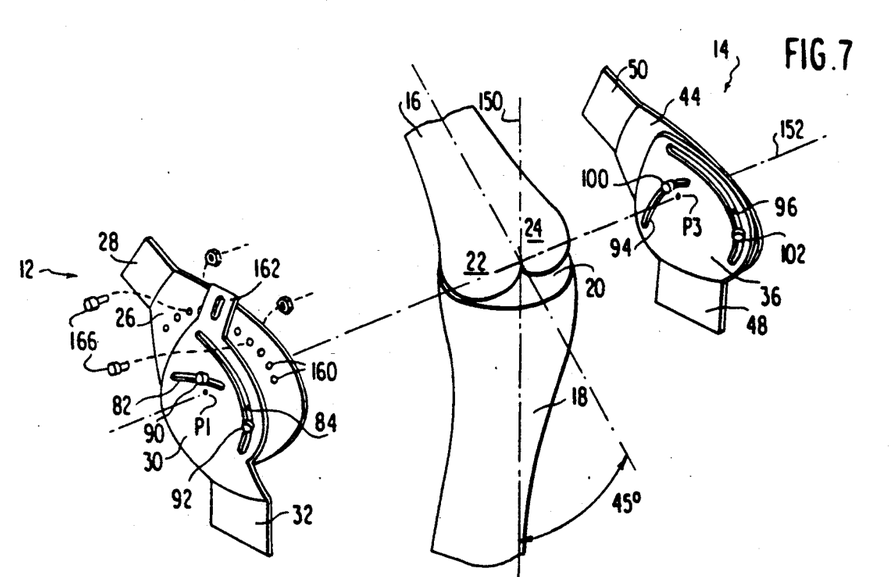
FIG. 7 is an exploded diagrammatic-schematic perspective view of the hinge showing the tibia with respect to the femur at 45° of flexion.

FIG. 7 depicts a flexion position of approximately 45° between the femur and the tibia. In this description, the tibia is shown as it flexes and rotates with respect to the femur. Of course, the tibia could be held stationary and the femur flexed as there is a degree of flexion in both. But, for purposes of clarity, FIG. 7 suggests a flexion of the femur with respect to the tibia. The various figures of FIG. 10 display this swinging movement.

The second of the four distinct movements inherent in the physiological motion of the knee is found in that the tibia rotates slightly counter-clockwise (viewed from the top of the right knee) with respect to the femur during flexion. This rotation can best be understood with reference to FIGS. 10A–10D. This is a figure of the right knee when viewed from the top. Note the counter-clockwise progression of the foot orientation D in the transverse plane as flexion continues from FIG. 10A to FIG. 10D, thus exhibiting rotation of the tibia with respect to the stationary femur.

The third distinct movement of the knee is the abduction/adduction motion. As the knee flexes, the tibia undergoes a side-to-side swinging movement in the coronal plane known as abduction/adduction. See arrows A—A in FIG. 1. As flexion begins, the tibia moves toward the midline (vertical axis) and at about 90 degrees the tibia moves then slightly back away from the midline until full flexion is reached.

The fourth distinct movement of the human knee is the posterior (backward) migration of the femur with respect to the tibia during flexion. This posterior migration is referred to as "rollback". In the human knee this motion is asymmetrical. The lateral femoral condyle's "rollback" is greater than that of the medial. This movement can be quantified in terms of millimeters. The mean rollback for the lateral femoral condyle is 24 mm whereas for the medial it is 10 mm. Naturally, as with all movements of the human knee, these are mean quantitative values but qualitatively relate to the anatomical phenomenon of "differential rollback." FIGS. 10A-10D demonstrate this phenomenon.

FIGS. 10A'-10D' are a schematic side view of the medial femoral condyle in relationship to the medial tibial plateau As the femur flexes on the tibia the condyle "rollsback" to contact a progressional more posterior point on the plateau $(A_1, A_2, A_3)$ This rolling distance traveled is approximately 10 mm in the mean (average) human knee.

FIGS. 10A"-10D" are a schematic side view of the lateral femoral condyle in relationship to the lateral tibial plateau. As the femur flexes on the tibia, the lateral condyle "rollsback" to contact a progressively more posterior point on the plateau $(B_1, B_2, B_3)$.

On this lateral side, the distance traveled is greater, approximately 2.4 times greater, than on the medial side. This difference produces the phenomenon of "differential rollback".

These movements are not in fact isolated but actually occur concurrently. The resulting motion is a complex composite of flexion-extension, internal-external rotation, absduction-adduction and "differential rollback". The prior art, heretofore, has not been able to accommodate this complex movement to accurately track the true anatomical motion of the knee. Reference to the various figures of FIG. 10 illustrates the relationship between these four basic movements. FIG. 10A shows the right knee at 0° flexion looking downwardly in the traverse plane. It shows foot orientation is slightly angled to the right FIG. 10A' is a side view of the medial femoral condyle and tibial plateau 10A" a side view from the lateral femoral condyle and tibial plateau. The letter A represents the point of contact of the medial condyle and the letter B the point of contact of the lateral condyle with surface 20.

Figure 10B:
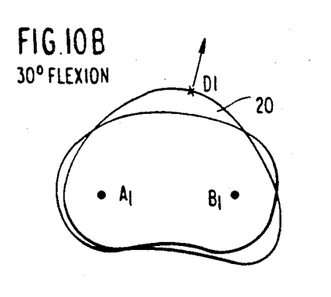

FIGS. 10B, 10B' and 10B" show position at 30° flexion. In FIG. 10B note that foot orientation has moved counterclockwise, exhibiting rotation, and the condyles have glided slightly backward so that their areas of contact remains generally central of the tibia plateau, thus exhibiting roll-back. At 30°, although the original areas of condyle contact with surface 20 have moved, the new points of contact A1 and B1 remain relatively constant with respect to surface 20.

Figure 10C:
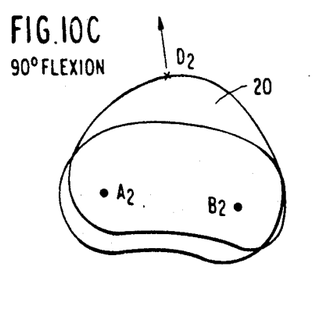
Figure 10D:
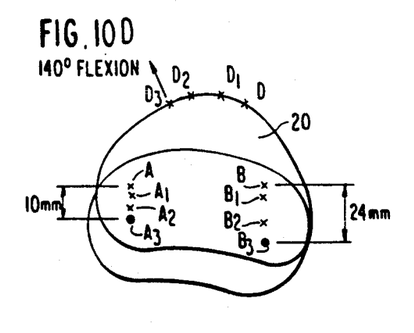

At 90° flexion, the areas of contact A2 and B2 move slightly rearwardly (FIG. 10C) Note that B2 (the lateral point of contact) has moved more than A2. Note that foot orientation has moved from slight external rotation (slewfoot) to slight internal rotation (pidgeon-toed). FIGS. 10C' and FIG. 10C" show that the lateral condyle has shifted posteriorly (backward) more than the medial condyle.

FIGS. 10D, 10D' and 10D" show position at 140° flexion. In FIG. 10D the foot orientation is in further internal rotation. The lateral condyle has shifted posteriorly (backward) further than the medial condyle as depicted in o FIGS. 10D, 10D', and 10D" as stated previously, this ultimate change from 0° flexion for the medial condoyle is roughly 10 min and for the lateral is roughly 24 mm.

The hinge herein presented is designed to produce an anatomically correct position for each degree of flexion with respect to the above four movements to closely mimic the natural state of the knee. The first distinct motion, the flexion/extension is accomplished through the path of rivets 90 and 92 in conjunction with rivets 100 and 102. For the purposes of the first distinct movement, the respective shells can be considered to be flat as only the projections in the sagittal plane have bearing on this motion. As noted above, the knee changing. Respective shell movement is restricted to that defined by the rivets and slots and thus produces the required polycentric movement.

As shown in FIG. 5, the center of rotation C of hinge member 30 at any time is determined by the intersection of the normal lines to the curves 82 and 84 at the points of rivets 90 and 92 respectively. Similarly, the center of rotation of hinge member 36 at any time is determined by the intersection of the normal lines to the curves 94 and 96 at the points of rivets 100 and 102 respectively. Given the changing degree of curvature of respective slots, the normal lines to these curves intersect at different points as flexion proceeds. Thus, although the centers of rotation of hinge members 30 and 36 remain fixed, the center of rotation of the upper hinge members 26 and 44 or—the centers of rotation of each hinge changes continuously. Since the overall axis of the brace is determined by the line which joins the centers of rotation of hinges 30 and 36, the end result is that the brace rotates about a constantly changing axis, closely approximating the actual movement of the human knee.

For example, at full extension, rivets 92 and 102 are at the lowest point of their paths, rivets 90 and 100 are at their frontmost positions, defining an axis of rotation for the brace which approximately lies on the condylar axis 152 at C1. As flexion begins, the rivets 92 and 102 begin moving up, (superiorly) while rivets 90 and 100 move rearwardly (posteriorly), leading to an axis of rotation which lies to the rear and below the original condylar axis 152 at C2.

The particular curve shapes necessary to accomplish polycentric motion which accurately tracks knee movement was determined empirically to be as shown in the drawings.

To accommodate the second distinct movement, rotation, the present hinge design provides a spherical component in hinge members 30 and 36 which produces a rotation during flexion between upper and lower brace portions FIG. 6 depicts the femur 16 disposed centrally of tibia plateau 20. The leg is in its unflexed or extended position. The femur 16 and the tibia 18 lie along the generally vertical axis 150. The centers of curvatures of the shell units are disposed along the transverse axis 152, which axis is also aligned with the transverse omit axis of condyles 22 and 24. Because of the spherical character of the shells, rivets 90, 92, 100, and 102 induce movement between the respective shells in the coronal plane during flexion. Note that, in the fully extended position, rivet 92 is at the lower (distal) end of slot 84, rivet 90 is at the forward (anterior) end of slot 82, rivet 102 is at the lower (distal) end of slot 96, and rivet 100 is at the upper (anterior superior) end of slot 94. Thus, when the hinges are viewed from the front of the right knee of the wearer, rivets 92 and 102 are located in their inward, (closer to the knee) locations and rivets 90 and 100 are located near the apexes of the shells and are at, or near, their outward positions (farthest from the knee). The differences in relative movement between hinges 30 and 36 produce the aforementioned rotation.

Figure 8:
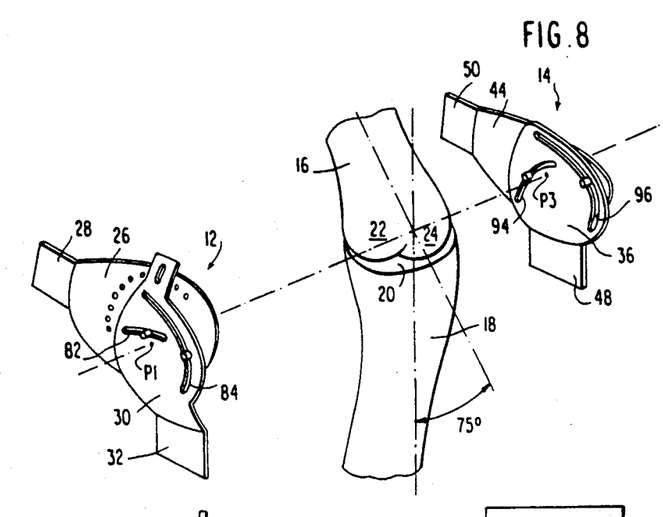
FIG. 8 is an exploded, diagrammatic-schematic perspective view of the hinge with the knee in its 75° flexed position.

Rotation can be best understood with reference to FIGS. 9A, 9B, and 9C hereinafter described. In FIGS. 4, and 4A, 5, and FIG. 5A apex reference points P1, P2, P3 and P4 are all colinear and aligned on the condylar axis with rivet positions as noted above. As flexion progresses, slots 84 and 82 guide reference points P1 and P3 out of alignment. At 45°, rivets 90 and 100 remain near the apex of the slots in their respective shells and rivets 92 and 102 are positioned more superiorly (upward) than before in accordance with the shape of slots 84 and 96. FIG. 8 shows a 75° flexion position. Here, the rivet 92 is positioned even more superiorly (upwardly) in its slot 84, and rivet 90 has moved midway of the length of slot 82 as the shell 30 moves. Also in FIG. 8 it can be seen that rivets 100 and 102 are relatively positioned along their respective slots. This displaces apex reference point P3 down with respect to its original position at "0" as shown in FIG. 9B. This downward displacement produces an angular displacement shown as alpha in FIG. 9B which represents the angle of rotation. During flexion, the tibia extensions 32 and 48 will remain substantially parallel to one another but will rotate in unison with respect to upper bracket portions 28 and 50. Thus the second distinct motion is accommodated.

The third basic knee motion, adduction/abduction is accommodated once again through the spherical contours of the shells. Adduction/abduction is produced where the vertical axes of lower shells 36 and 32 are displaced from the sagittal plane. FIG. 9C represents such a displacement. As lower shells 30 and 38 are displaced backwardly (posteriorly) the rivets 92 and 102 are positioned upwardly (superiorly) in their slots. This can be seen in FIG. 9C as reference apex P3 has been displaced away from apex P4. This displacement causes extension member 48 to adduct in the coronal plane in relation to extension member 50. The extent of that movement is represented by the angle beta (FIG. 9C). A similar movement occurs in the other shell-pair. The converse of this adductive movement occurs upon extension, thus producing an abductive movement.

The fourth distinct motion, "rollback" is provided by the present hinge design. The slots are shaped so as to cause the wearer's leg to follow normal movement of the knee insofar as "roll-back" is concerned. It should be noted that in full extension (FIG. 6) the slot 82 is generally crossways of shell 30 whereas slot 94 of shell 36 is almost vertical. Because of this differential effect, movement is greater on the lateral side of the knee than it is on the medial side to accommodate "differential rollback". The generally horizontal slot 82 permits greater rotational movement about the knee on the lateral side whereas the vertical slot 94 restrains rotation on the medial side movement. The above mentioned polycentric rotation completes the accommodation of "rollback". As the center of rotation changes, the femur condyles are guided posteriorly to closely mimic the actual movement of the knee.

FIG. 7 shows a series of apertures 160 are formed in shell 26. These apertures are located along a path followed by an upwardly (superiorly) extending lug 162 of shell 30. The apertures and slots are adapted to receive a nut and bolt and used to prevent any movement in the hinge. More commonly, stop cams 166 are inserted into apertures on either side of lug 162. This limits the movement of shell 30 with respect to shell 26 to the area between stop cams 166. Thus, the attending physician can adjust the degree of movement permitted during each stage of rehabilitation.

It should be understood that rotation, roll-back, and adduction/abduction during flexion are not directly proportional to one another. For instance, in the first few degrees of flexion rotation occurs rapidly, then rotation lessens. Likewise, there is little roll-back in the initial stages of flexion but the backward motion increases. Additionally, rolling motion of the external femial condyle in the lateral plateau is greater than that in the medial side; giving rise to the aforementioned "differential roll-back". This phenomenon is produced by the simultaneous gliding (spinning) within of the medial femerial condoyle on the medial plateau being nearly twice as rapid as in the lateral side. The slots are shaped to follow these movements.

Figures 3, 4A:
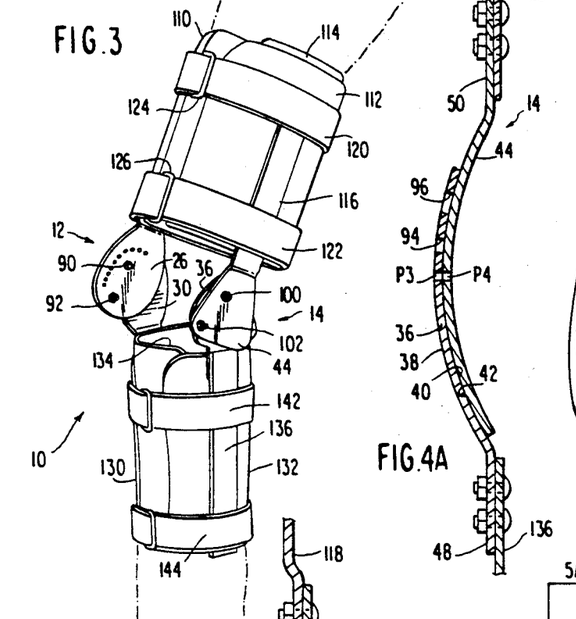
FIG. 3 is a perspective view of a brace for the right leg of the wearer.
FIG. 4A is a cross-sectional view along the lines 4A—4A of FIG. 4.
Figure 4:
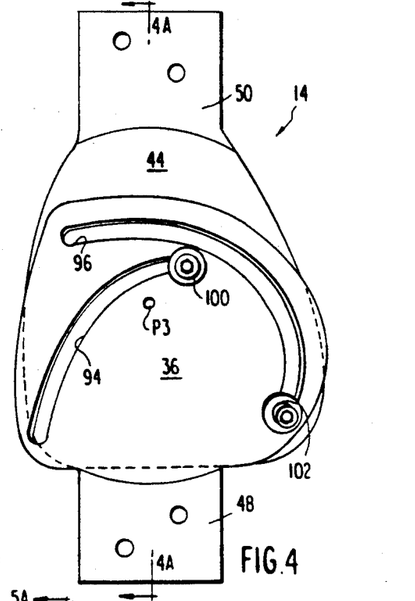
FIG. 4 is a side interior elevational view of the medial (inner) leg hinge component of FIG. 3.
Figure 9A:
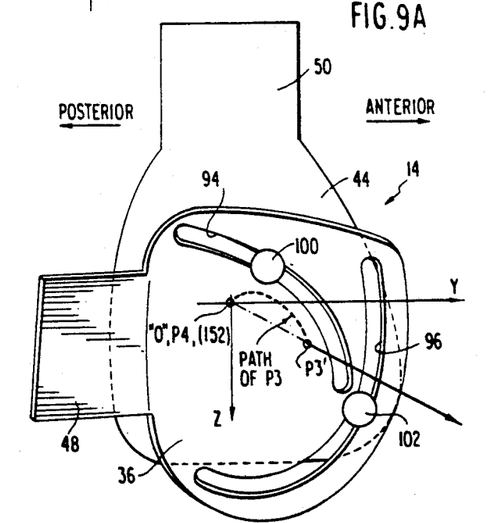
FIGS. 9A, 9B, and 9C are diagrammatic views illustrating how the curvilinear components account for abduction/adduction and rotation during knee flexion.
Figure 9B:
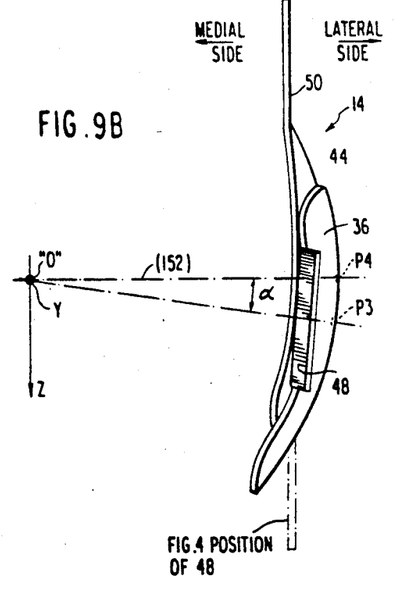
Figure 9C:
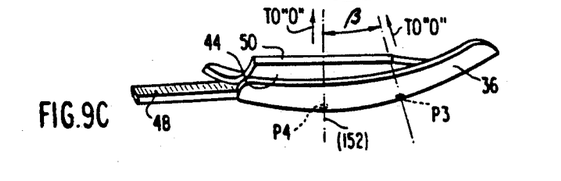

FIGS. 9A, 9B, and 9C are illustrative of the tracking movements of the present device and can best be understood by noting the movement of P1 with respect to P2 and P3 with respect to P4. In the position of FIG. 4A, P3 and P4 are aligned and located on a line perpendicular to the drawing plane, which line also passes through the center of the mating spherical surfaces. As shell 36 "rotates" as controlled by slots 94, 96, P3 is displaced forwardly in the Y direction and downwardly in the Z direction as shown in omit and 9. Axis O-P3 originally perpendicular to the plane of the drawing is now tilted (see line O-P3'). Thus, it can be seen that abduction/adduction is tracked by a movement of shell 36 along the Y axis. As shown, this measurement is angle B in FIG. 9C. Rotation, on the other hand, is tracked by the movement of shell 36 in the direction of the Z axis. This angular measurement is labeled as angle alpha in FIG. 9B.

While there has been disclosed an effective and efficient embodiment of the invention, it should be well understood that the invention is not limited to such an embodiment as there might be changes made in the arrangement, disposition and form of the parts without departing from the principle of the present invention as comprehended within the scope of the accompanying claims.

We claim:

1. A brace for attachment to a wearer's leg, for controlling abduction/adduction and the differential rollback movement of the knee comprising:

first and second thigh cuffs on the lateral and medial sides of the wearer's thigh;

first and second calf cuffs on the lateral side and medial side of a wearer's calf;

a lateral hinge component disposed on the lateral side of the wearer's knee;

a medial hinge component disposed on the medial side of the wearer's knee;

a linkage between said lateral hinge and said first thigh cuff;

a second linkage between said lateral hinge and said first calf cuff;

a third linkage between said medial hinge and said first calf cuff; and a fourth linkage between said medial hinge and said second calf cuff;

said lateral and medial hinges having respective first and second axes that are coincident when said leg is unflexed and in alignment with the transverse condylar axis of the wearer's leg; and control means to maintain said first axis in a relatively fixed position concentric with said transverse condylar axis of said wearer's knee and to permit movement of said second axis as said abduction/adduction and differential rollback movements occur; and wherein said lateral hinge means has:

a first spherical shell connected to said first linkage, a second spherical shell in nesting relationship with said first shell and connected to said second linkage;

said medial hinge means has a third spherical shell connected to said third linkage and a fourth spherical shell in nesting relationship with said third shell and connected to said fourth linkage; and said control means includes slots in said first shell that receive rivets fixedly secured to said second shell and second slots in said third shell that receive rivets fixedly secured to said fourth shell.

2. A knee brace appliance for tracking the movement of the knee joint, said brace being of a type having first and second gripping means to grip, respectively, the wearer's leg above and below the knee and a connecting hinge means therebetween along the lateral and medial sides of the knee, comprising:

a first spherical shell disposed with its concave surface facing the said knee;

linkage means securing said first spherical shell to said first gripping means so that the center axis of said shell is concentric with the center axis of the wearer's condyles when the wearer's leg is in full extension.

a second spherial shell having a convex surface in mating relationship with said concave surface of said first shell and having a second center axis aligned along center axis of said condyles when the wearer's leg is in full extension;

a third spherical shell disposed with its convex surface facing said knee;

said linkage means securing said third spherical shell to said first gripping means so that the center axis of said third shell is concentric with the center axis of the wearer's condyle when the wearers leg is in full extension;

a fourt spherical shell having a concave surface in mating relationship with said convex surface of said third shell and third shell having a center axis alignment with the axis of said third shell when the wearer's leg is in full extension;

first interengaging control means between said first and second shells; and second interengaging control means between said third and fourth shells causing said second concentric axis to maintain alignment with said axis of said condyles during flexion and extension as the tibia moves with respect to the femur and wherein said first and second interengaging means include slots formed in said first and third shells that receive pins extending from said second and third shells.

3. The invention of claim 2 wherein said interengaging means is comprised of slots formed in said first and third shells that receive rivets affixed to said second and fourth shells.

4. The invention of claim 3 wherien said slots are shaped to follow the differential roll-back movement between the condyles and the tibia and the concavity of said shells causes said appliance to track the rotation, adduction and abduction movement of the wearer's knee.

5. A leg brace of a type for securement to the leg of a wearer to track the relative movements of abduction/adduction, rotation, and differential roll-back between the femur and the tibia during flexion and extension comprising:

first and second thigh extensions adapted to be placed on the medial and lateral sides of the thigh in general parallel alignment with the femur;

means affixing said extensions to said thigh to prevent relative movement therebetween;

first and second calf extensions adapted to be placed on the medial and lateral sides of the calf in general parallel alignment with the tibia;

second means affixing said extensions to said calf to prevent relative movement therebetween;

a first hinge adapted to be placed on the lateral side of the knee connecting said first thigh and said first calf extension;

a second hinge adapted to be placed on the medial side of the knee connecting said second thigh and calf extension; and cooperative means in said first and second hinges causing said brace to track said differential roll-back, rotative, and abduction/adduction movements of the leg during flexion and extension.

6. The invention of claim 5 wherein said cooperative means includes slot and pin interengaging members.

7. The invention of claim 5 wherein said cooperative means further includes a series of spherical shells having their respective convex surfaces all facing in the same direction.

8. A brace for a knee joint wherein upon flexion and extension of the femur with respect to the tibia, there occurs an abduction/adduction movement, a rotational movement and a differential rollback movement, the improvement comprising:

a first brace element fixedly secured to the thigh of a wearer;

a second brace element fixedly secured to the calf of the wearer;

hinge mechanisms on the lateral and medial sides of said knee joint and connecting said first brace element to said second brace element, said hinge mechanisms including;

first means of said hinge mechanisms to track a lateral to medial movement during said flexion and extension;

second means of said hinge mechanism to rack said differential roll-back during said flexion, and extension; and third means of said hinge mechanism to track said rotational movement during said flexion and extension.

9. The invention of claim 8 wherein said first and second hinge elements are respectively formed with arcuate slots and said third and fourth hinge elements are respectively formed with pins that are received by said slots and said means for tracking said differential rollback are said pins and slots.

10. The invention of claim 9 wherein said means to track said abduction-adduction is the shape of said elements.

11. The invention of claim 9 wherein said means to track said abduction/adduction is the spherical shape of said elements.

12. The invention of claim 9 wherein said means to track said rotation is the shape of said elements.

13. An anatomical bracing hinge apparatus comprising:
a first shell, having a convex spherical surface of a first radius;
a second spherical shell having a concave surface having a radius equal to said first radius and in close sliding relationship with said convex surface of said first shell and one of said shells having a plurality of slots formed therein;
a plurality of rivets extending from the other of said shells, one each of said rivet extending through one each of said slots;
said first and second shells adapted to be placed on the lateral side of a wearer's knee joint;
a third shell having a convex spherical surface having a second radius;
a fourth spherical shell having a concave surface having a radius equal to said second radius and in close sliding relationship with the convex surface of said third shell and one of said third or fourth shells having a plurality of second slots formed therein;
a plurality of second rivets extending from the other of said shells one each of which extends through one of said second slots;
said third and fourth shells adapted to be placed on the medial side of a wearer's knee joint opposite said first and second shell; and
wherein said convex spherical surface of said first shell and said convex spherical surface of said second shell face in the same direction and said convex surface of said third shell and said convex surface of said fourth shell also face in said direction.

14. The invention of claim 13 wherein heads are formed on the ends of said rivets to maintain said shells in engagement with one another.

* * * * *